(12) United States Patent
Hochrainer et al.

(10) Patent No.: US 7,708,011 B2
(45) Date of Patent: May 4, 2010

(54) DRY POWDER INHALER

(75) Inventors: Dieter Hochrainer, Oberkirchen (DE); Joerg Schiewe, Mainz (DE); Bernd Zierenberg, Bingen (DE); Stephen Dunne, Suffolk (GB)

(73) Assignee: Boehringer Ingelheim Pharma GmbH and Co. KG, Ingelheim am Rhein (DE)

( * ) Notice: Subject to any disclaimer, the term of this patent is extended or adjusted under 35 U.S.C. 154(b) by 0 days.

(21) Appl. No.: 10/669,576

(22) Filed: Sep. 24, 2003

(65) Prior Publication Data

US 2004/0187868 A1 Sep. 30, 2004

(30) Foreign Application Priority Data

Sep. 26, 2002 (DE) ................. 102 44 795

(51) Int. Cl.
*A61M 15/08* (2006.01)
*A61M 11/00* (2006.01)

(52) U.S. Cl. ............... 128/200.14; 128/203.24; 128/204.24; 128/204.25; 128/203.12; 128/203.14; 128/203.19; 128/203.15; 128/203.21

(58) Field of Classification Search ............ 128/200.11, 128/200.14, 200.16, 200.18, 200.23, 203.15, 128/203.19, 203.21, 203.24, 205.24, 200.15; 239/398, 399, 401, 407, 411
See application file for complete search history.

(56) References Cited

U.S. PATENT DOCUMENTS 2,693,805 A * 11/1954 Taplin et al. ........... 128/203.15
3,698,390 A * 10/1972 Ferris .................... 128/202.13
4,634,053 A * 1/1987 Herzfeld et al. ............. 239/315
4,702,415 A 10/1987 Hughes
5,083,429 A * 1/1992 Veres et al. .................. 60/325
5,147,087 A * 9/1992 Fuchs ......................... 239/333
5,546,932 A 8/1996 Galli
5,967,164 A 10/1999 Denda et al.
6,089,228 A * 7/2000 Smith et al. ............ 128/203.15
6,415,991 B1 * 7/2002 Eriksson .................... 239/290

(Continued)

FOREIGN PATENT DOCUMENTS

DE 196 43 054 A1 4/1998

(Continued)

OTHER PUBLICATIONS

Webster's II New Riverside University Dictionary, definition of "cartridge".*

(Continued)

*Primary Examiner*—Justine R Yu
*Assistant Examiner*—Clinton Ostrup
(74) *Attorney, Agent, or Firm*—Michael P. Morris; Mary-Ellen M. Devlin; David L. Kershner

(57) ABSTRACT

A dry powder inhaler (1) is to be made available, with which a particle size and particle size distribution preferred for inhalation are to be achieved and by means of which as high a line particle fraction as possible is to be realized. This is achieved by means of a dry powder inhaler (1) that is characterized in that provided in the inhaler (1) is a nozzle (10) through which the aerosol (9) flows before leaving the inhaler (1).

19 Claims, 3 Drawing Sheets

U.S. PATENT DOCUMENTS

| | | | |
|---|---|---|---|
| 6,443,152 B1 * | 9/2002 | Lockhart et al. | 128/203.21 |
| 6,488,648 B1 * | 12/2002 | Matsugi et al. | 604/57 |
| 6,513,345 B1 * | 2/2003 | Betting et al. | 62/637 |
| 6,595,210 B2 * | 7/2003 | Ohki et al. | 128/203.15 |
| 6,663,848 B2 * | 12/2003 | Schiewe et al. | 424/46 |
| 6,799,571 B1 * | 10/2004 | Hughes et al. | 128/203.12 |
| 2001/0029948 A1 * | 10/2001 | Ingle et al. | 128/203.15 |
| 2001/0055709 A1 * | 12/2001 | Sang | 429/34 |
| 2004/0035421 A1 * | 2/2004 | Schuckmann | 128/203.15 |
| 2004/0124269 A1 * | 7/2004 | Dushkin et al. | 239/399 |

FOREIGN PATENT DOCUMENTS

| | | |
|---|---|---|
| WO | WO 90/07351 | 7/1990 |
| WO | WO 92/04066 | 3/1992 |
| WO | WO 92/04928 | 4/1992 |

OTHER PUBLICATIONS

International Search Report for PCT/EP03/09850 mailed Dec. 9, 2003.

* cited by examiner

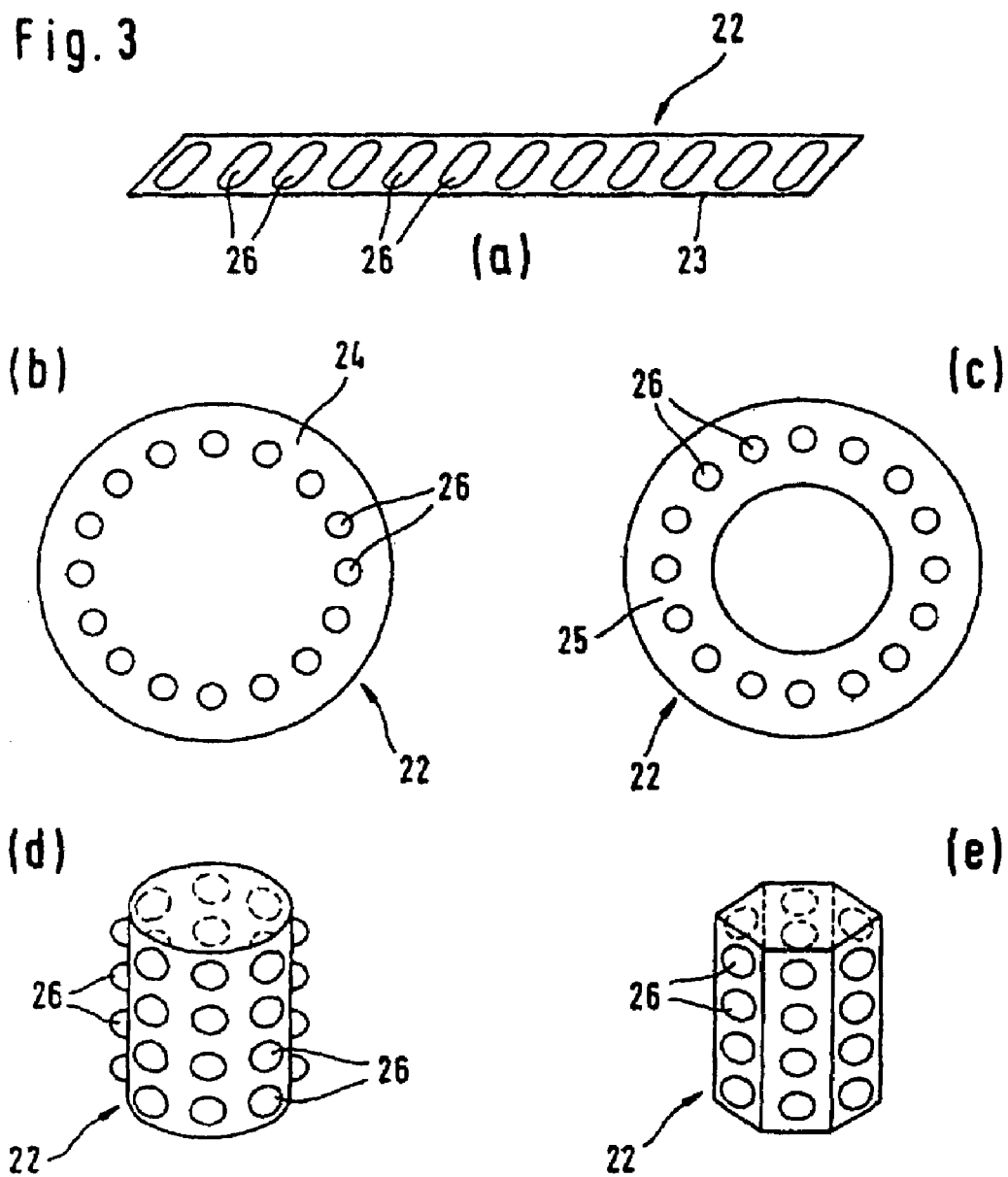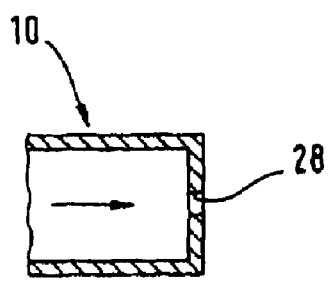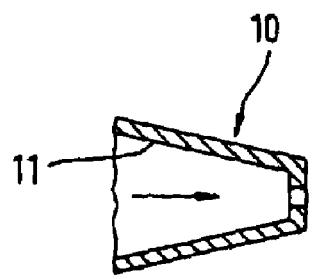

DRY POWDER INHALER

The invention pertains to a dry powder inhaler with a mouthpiece for dispersing pharmaceutical drug formulations, having an auxiliary energy source in the form of a pressure medium system, with a device for provisioning of a powder formulation, whereby upon activation of the pressure medium system a gaseous pressure medium released by the pressure medium system forms with the powder formulation an aerosol in such a way that the powder particles are present in dispersed form within the gaseous pressure medium.

Such dry powder inhalers are needed for providing inhalable drugs. Particularly in the case of diseases in the lung and bronchial region, the drugs are needed and are made available in the form of inhalable drugs (inhalants).

In the context of the present invention, the term "drug" should be understood as the active component of a drug, which is usually termed the active drug or active ingredient as well.

In principle, the term "drug formulation" also includes solution formulations and suspension formulations along with powder formulations. A variety of inhalation systems have been developed for each type of formulation. The solution or suspension formulations are formulated in a pharmacologically suitable solvent. Basically, water or liquefied propellant gases, for example, are used as the solvent. In the past, fluorochlorohydrocarbons were used, and more recently, fluorohydrocarbons. In the case of such inhalers that are operated with slightly volatile propellant gases, the drug is also formulated as a solution or suspension within the propellant.

In the context of the present invention, the powder formulation, or more specifically, the dry powder inhaler needed for its dispersion, are in the foreground. However, it should be noted at this point that the three different drug formulations with their special properties place entirely different demands on the inhaler.

In inhalers, the formulations are usually stored or provisioned in a reservoir, for which reason the formulations that are being used must exhibit adequate storage stability. For that purpose, it is possible to add to the drug excipients, by means of which the physical and chemical properties that influence quality-determining parameters, such as availability and shelf-life, can be adjusted in the desired way.

The drug formulation that is provisioned in a dry powder inhaler is pulverized and is inhaled as an aerosol by the patient. In conjunction with this, the drugs are made available in inhalable form.

Normally, however, the entire measured dose is not output as an aerosol, but only a portion of it. That is due to the fact that a portion of the powder formulation remains behind in the supply vessel, is only swirled up and then deposited again in other places inside the inhaler.

That portion of the measured dose that leaves the mouthpiece of the inhaler is called the output dose.

During the inhalation process, powder particles can get into the lungs only if the aerodynamic particle diameter is less than 5 µm. The consequence is that only a portion of the output dose can actually get into the lungs. This portion can be determined only by means of elaborate experiments on the patient. For that reason, in vitro tests have been developed by means of which a simple laboratory experiment can be used to determine the aerodynamic fine fraction, which correlates to the respirable portion of the output dose. The aerodynamic fine fraction is defined as that portion of the measured dose, in percent, that possesses an aerodynamic particle diameter of less than 5.8 µm.

In the context of the present invention, aerodynamic particle diameter is understood to mean the particle diameter that corresponds to the equivalent diameter of a sphere with a density of 1 $g/cm^3$ that possesses the same sedimentation speed in air as the studied particle.

The following considerations are helpful for obtaining as high a fraction of aerodynamic fine particles as possible.

First, a powder formulation must be provided that contains the drug in micronized form. The preponderant portion of all drug particles should have a size in the range between 1-5 µm. Since micronized powders in the form of bulk products display a great tendency to form particle agglomerates, the powder formulation usually contains excipients that facilitate the deagglomeration of the micronized drug particles as well as increasing the flowability. Another quality-related parameter for a powder formulation is its chemical and physical stability. Chemical stability is given if the drug is not converted into decomposition products during storage. Physical stability pertains to the fact that the measured aerodynamic fine fraction does not change during the storage period.

A suitable dry powder inhaler must convert a defined amount of the powder formulation, the measured dose, into an aerosol form during the patient's inhalation process, whereby values as high as possible should be attained for the output dose and the aerodynamic fine particle fraction. To achieve that, one important function of the dry powder inhaler is to deagglomerate as efficiently as possible the particle agglomerates that are present in the bulk product of the powder formulation, since larger particles are already deposited in the mouth and throat regions during inhalation, and only particles with aerodynamic particle diameters of less than 5 µm get into the lungs. This results in a more or less large difference between the portion of the output dose relative to the measured dose and the aerodynamic fine particle fraction, which is decisively influenced by the efficiency of the pulverization.

Against the background of the remarks made above, it must be possible to reproduce the particle size within narrow limits so that fluctuations in the output dose and in the aerodynamic fine fraction are avoided. An approximately same-sized amount of the drug should be administered with every actuation of the inhaler, whereby the output doses should have approximately the same drug particle size distributions.

However, from the standpoint of efficiency and as economic a handling of drugs as possible, the creation of as large an aerodynamic fine particle fraction as possible—as defined above—is also sought.

Basically, according to the state of the art two different systems of dry powder inhalers are used.

So-called passive inhalers usually use the patient's inhaled air to pulverize the powder formulations without using any additional auxiliary energy sources—such as compressed air, for example. These dry powder inhalers are designed in such a way that the powder is either contained in the form of a single dose (premetered dose) in a ready-made capsule, or else several predosed amounts are made available in a multidose container that is inserted into the inhaler. During use, the capsule or one of the multidose containers is punctured, whereby the emptying and pulverization of the powder takes place by means of the air inhaled by the patient.

The powder can also be present in the inhaler in the form of bulk powder, whereby an individual dose is made available by means of a dosing device before it is transported out of the inhaler by the breathing air of the patient.

It is apparent that with the described dry powder inhalers, the aerodynamic fine particle fraction is strongly dependent on the breathing maneuver of the patient.

Against the background of the remarks made above, a transition has been made to the use of so-called active dry powder inhalers, which have stored energy available, e.g., compressed gas. By using the compressed gas for a defined output and pulverization of the powder formulation, independence from the patient's breathing maneuver is obtained.

In the state of the art, essentially two paths were taken in order to bring about deagglomeration and efficient pulverization, and to obtain the desired particle size and particle size distribution.

In some of the inhalers described in the literature, the deagglomeration of the powder is supported by the collision of the particles against so-called collision surfaces. For example, with the aid of pressure, the powder particles are directed against these collision surfaces in a purposeful fashion in order to achieve deagglomeration of the particles. However, this then has the effect that some of the powder particles that strike the collision surface remain adhered to the collision surface and become lodged there. This has the result of making it impossible to achieve dosing that is as accurate and reproducible as possible.

Disadvantageous is the fact that with the use of pressurized gases for the deagglomeration of powder formulations, very high aerosol speeds are generated. Very high aerosol velocities in turn lead to the fact that the portion of the dose that reaches the lungs is reduced. As a result, additional spacers/separators that had the task of reducing the speeds of the aerosol particles formed were provided for dry powder inhalers that work with compressed gases.

These spacers/separators (or deagglomeration chambers) in which the speed of the powder particles is decelerated are placed in front of the mouthpiece of the inhaler, making the inhaler cumbersome and unwieldy. Inhalers for the pharmaceutical industry should be small and handy, however, so the patient can always have the inhaler with him.

Against this background, the task of the present invention is to make available a dry powder inhaler for the dispersing of pharmaceutical powder formulations, with which the problems known from the state of the art of conventional dry powder inhalers are eliminated or at least alleviated, and in particular, with which a high fraction of solid particles less than 5.8 μm can be generated.

This task is solved through a dry powder inhaler of the generic type, which is characterized in that provided in the inhaler is a nozzle through which the aerosol flows before leaving the inhaler.

In the dry powder inhaler according to the invention, the pressure medium carries the powder from the powder provision and transports it through the nozzle.

In conjunction with that, the gaseous pressure medium is accelerated more strongly, and the powder particles contained in it are also carried along by it, and the deagglomeration of the powder particles takes place as a result. The shear forces exerted on the particles by the gaseous pressure medium as a result of the higher gas molecule speeds cause a breakup of the particle agglomerates as this takes place.

In its simplest embodiment, the nozzle is a so-called aperture plate. The deagglomeration efficiency was measured by means of the aerodynamic particle size distribution of the particles with the aid of a cascade impactor. The fine particle fraction as a percentage of the predosed powder amount was specified as the critical measured value. For this purpose, 5 mg of micronized Fenoterol HBr was used as the drug each time. Indicated below is the measured fine particle fraction for this nozzle variant.

TABLE 1

| Nozzle | Diameter [mm] | Compressed Air Volume [ml] | Pressure [bar] | Fine particle fraction [%] |
|---|---|---|---|---|
| Aperture plate | 0.4 | 12 | 4 | 44 |
| Aperture plate | 0.6 | 7.5 | 4 | 34 |
| Aperture plate | 0.8 | 12 | 0.5 | 42 |

A HandiHaler® brand inhaler was used as the reference. Such a device is described in EP 0911047, for example, This inhaler (HandiHaler) is intended for the inhalation of powdered drugs from capsules. It is characterized by a housing, containing two windows, a deck in which air intake openings are located and which is provided with a screen fastened over a screen housing, an inhalation chamber, which is connected with the deck and on which is provided a push-piece that is equipped with two ground needles and can be moved against a spring, and a mouthpiece that can be folded over an axis and that is joined with the housing, the deck and a cap. With an air quantity of 4 liters and a pressure drop of 4 kPa, this device delivers a fine particle fraction of 18-20% of a predosed amount of 5 mg of Fenoterol HBr. The values in Table 1 thus illustrate the markedly higher deagglomeration efficiency of the described system according to the invention.

If an aperture plate is used as the nozzle, apertures with a diameter of 0.1 to 3 mm, preferably 0.3 to 2 mm, in particular, 0.5 to 1.5 mm, are used.

In another embodiment of the dry powder inhaler, the nozzle is not just a simple aperture plate; instead, the plate exhibits an inlet section that narrows. This nozzle can be further developed so that the outlet section widens in addition, so that the nozzle exhibits the shape of a tube that narrows in the middle and in which the angle of the narrowing tube section that originates as a result of the constriction can be the same or different. A continuously narrowing inlet section or widening outlet section ensures constant acceleration or deceleration of the aerosol stream. The flow lies in laminar fashion against the inner wall of the nozzle, and any forming of turbulent zones and so-called "dead water zones" in which the aerosol flow stands and no longer flows, i.e., the flow to a certain extent comes to a standstill, is prevented. The prevention of "dead water zones" should be viewed as particularly advantageous in terms of the precipitation of powder particles.

In the case of nozzles with a converging inlet section and a hole-like outlet, i.e., without a diverging outlet, holes with a diameter of 0.1 to 3 mm, preferably 0.3 to 2 mm, in particular, 0.5 to 1.5 mm, are preferred.

In the case of nozzles with a converging inlet section and a diverging outlet section, the narrowest cross sections with a diameter of 0.1 to 3 mm, preferably 0.3 to 2 mm, in particular, 0.5 to 1.5 mm, are preferred.

In the design of a nozzle with a converging inlet section and a diverging outlet section, the inlet opening of the nozzle has a diameter that is preferably 2 to 6 mm, in particular, 3 to 5 mm. The inlet section has a concave or linear course with an angle of opening of preferably 10 to 50°. The inlet section preferably has a length of 3 to 10 mm, preferably 5 to 8 mm.

In the case of nozzles with a diverging outlet, the opening of the outlet section preferably has a diameter of 0.1 to 10 mm, especially preferably 0.3 to 7.5 mm, very especially preferably 0.4 to 5 mm. The angle of opening of the outlet section is 7 to 15°, preferably 8 to 12°. However, the shape of the outlet section can also be characterized by a linear divergence followed by a tubular section. Its length is preferably 3 to 50 mm, especially preferably 5 to 15 mm.

Dry powder inhaler embodiments in which the nozzle is a Laval nozzle are especially advantageous in that regard.

In this embodiment of the dry powder inhaler, the aerosol flows through the nozzle, whereby it first enters the narrowing inlet section, passes through the middle piece, in which the narrowest cross section of the nozzle is placed, and then flows through the widening outlet section.

In conjunction with this, the aerosol accelerates in the narrowing inlet section, whereby the gaseous pressure medium is again accelerated more strongly and carries along with it the powder particles it contains, as a result of which the transport of the powder particles takes place. The shear forces exerted on the particles by the gaseous pressure medium as a result of the higher speeds of the gas molecules cause a breaking up of the particle aggregates/agglomerates into smaller particles of less diameter, as a result of which a deagglomeration is achieved. The aerosol reaches its highest speed in or after the narrowest cross section of the nozzle, which is located in the middle piece.

Gas speeds below or above the speed of sound are generated in the Laval nozzle, depending on the pressure that is being applied.

The gas speed relative to the speed of sound is designated as the Mach number (Ma). The Mach number is calculated as the quotient of the gas speed and the speed of sound. Thus Ma=1 if the gas speed that is reached has attained the speed of sound. The term supersonic speed is used if Ma>1.

Embodiments of the nozzle are advantageous if they are of a type such that the pressure medium is accelerated to supersonic speed in the outlet section.

This assumes that the aerosol flow in the narrowest cross section of the nozzle has already reached the speed of sound. In that case, in which the aerosol reaches the speed of sound in the middle piece, i.e., Ma=1, the aerosol flow in the widening outlet section of the nozzle is additionally accelerated to supersonic speed.

The speed that is actually achieved in the widening outlet section of the nozzle—i.e., the Ma number—is significantly dependent on the pressure that is provided upstream of the nozzle. In this regard, the powder particles are not accelerated to supersonic speed as the gas molecules are, so that a difference in speed results that in turn leads to the fact that shear forces are exerted on the powder particles and they are deagglomerated.

In this embodiment, this leads to the forming of a so-called Mach shock in the region of the widening outlet opening. When the gas molecules pass through this Mach shock, within a very short distance of only a few millimeters the gas molecules are severely decelerated to subsonic speed. The powder particles, which were slower than the gas molecules before passing through the Mach shock, are decelerated less strongly than the gas molecules, so that after the Mach shock the powder particles exhibit a higher speed than the gas molecules. This leads to extremely high frictional and shear forces, which act upon the powder particles. The result is further deagglomeration of the particles, which leads to even better inhaler performance based on the particle sizes and particle size distribution that arise.

In the following, the measured fine particle fraction for 5 mg Fenoterol HBr, micronized, is shown for several Laval nozzle variants.

TABLE 2

| Nozzle | Diameter [mm] | Compressed Air | | Fine particle fraction [%] |
| --- | --- | --- | --- | --- |
| | | Volume [ml] | Pressure [bar] | |
| Laval nozzle | 0.5 | 7.5 | 4 | 30 |
| Laval nozzle | 0.8 | 7.5 | 4 | 26 |
| Laval nozzle | 1.5 | 7.5 | 4 | 32 |

Reference values: See Table 1.

Since too high a flow speed reduces the fine particle fraction that can reach the patient's lungs during an inhalation process, the speed at the outlet of the mouthpiece should be no greater than 20 m/s, preferably no greater than 10 m/s, in particular, no greater than 5 m/s.

Since high flow speeds have to be generated for the deagglomeration of the powder when passing through a nozzle, it is generally necessary to reduce the aerosol speed on the path section between the nozzle and the mouthpiece. This can be done in a variety of ways, so that it is possible to forego the use of the dry powder inhaler according to the invention along with a spacer. Specifically, this preferably results in the following:

The aerosol leaving the nozzle outlet can be mixed in a variety of ways with the patient's breathing air on the path section between nozzle and mouthpiece.

The creation of a swirling flow of the patient's inhalation air is a suitable measure for doing this. The aerosol cloud that passes through the nozzle is injected into the swirl of the inhalation air, as a result of which the forward components of the speed of the aerosol cloud are reduced.

A design of the nozzle in such a way that the inhalation air and the aerosol flow leaving the nozzle run in opposite directions, as a result of which a deceleration can be achieved as well, represents another measure for reducing the flow speed of the aerosol cloud.

In an alternative embodiment, the inlet opening of the inhalation air is located inclined or perpendicular to the direction of flow of the nozzle.

Below, the measured aerosol speed of the fine fraction at a distance of 10 cm behind the nozzle is given for two different measures and various nozzles (Table 3).

TABLE 3

| Nozzle | Diameter [mm] | Compressed Air | | Aerosol Speed [m/s] |
| --- | --- | --- | --- | --- |
| | | Volume [ml] | Pressure [bar] | |
| Aperture plate | 0.8 | 2.5 | 4 | 19 |
| Aperture plate | 0.6 | 6.7 | 1.5 | 12 |
| Aperture plate | 0.6* | 5.4 | 1.5 | 5 |
| Aperture plate | 0.6** | 5.4 | 1.5 | 2 |
| Aperture plate | 0.4 | 16.7 | 0.5 | 3 |
| Laval nozzle | 0.5 | 5.4 | 1.5 | 2 |

*Creation of a swirling flow of the patient's inhalation air.
**Inhalation air and the aerosol flow leaving the nozzle run in opposite directions.

In order to reduce the speed of the aerosol cloud leaving the nozzle inside the inhaler, it has proven to be advantageous to mix this aerosol cloud with an oncoming air stream. When doing this, it is advantageous if this oncoming air stream is generated by the user's inhalation process. With a dry powder inhaler, care is usually taken that the patient also inhales air when inhaling the powder cloud in order to be able to assure a complication-free inhalation process. To do this, air slots through which the patient also automatically inhales air when inhaling the particle cloud can be configured in the mouthpiece, for example. Within the context of the dry powder inhaler according to the invention, these air inlet openings can be configured in such a way that the incoming air runs opposite the aerosol cloud, as either a purely opposing air stream or as an air stream that collides with the aerosol cloud, thereby slowing its speed. In terms of design, this task can be solved in that the mouthpiece, for example, stands perpendicular to the path that the aerosol cloud takes when leaving the nozzle opening. The air inlet slots are then also designed perpendicular to the mouthpiece and in line with the exit path of the aerosol cloud when leaving the nozzle, but exactly opposite to the nozzle. Expressed in a simplified way, such a design would have the shape of a T-piece, whereby the nozzle for the aerosol cloud and the air inlets for the opposing air each define one end of the T-beam, and the mouthpiece corresponds to the foot of the T.

In an alternative embodiment, the nozzle and the air inlet holes empty into a swirl chamber, are swirled into each other there, and then emerge through a mouthpiece.

Such a swirl chamber in the simplest case can be a hollow space in which the nozzle discharges at one location: the air inlets can then empty into the space exactly opposite the nozzle, or preferably perpendicular to it, or at least offset at an angle. The space then has an outlet to the mouthpiece. In doing this, an imaginary line coming from the nozzle opening and an imaginary line from the mouthpiece entering the space form a straight line or they meet at an angle or they are collinear with each other.

In the simplest case, the dry powder inhaler according to the invention consists of a housing with a mouthpiece. Placed in front of the mouthpiece in the interior of the housing is the nozzle described above. Located further in the interior is a space for holding the powder formulation that is to be pulverized.

The dry powder inhaler preferably exhibits a pressure system that directs a pressurized gas to the quantity of powder formulation that is to be dispersed so that the latter is dispersed and the resulting aerosol is directed into the mouthpiece through the nozzle system described above, breaking up the coarser particles. In conjunction with this, in its interior the dry powder inhaler exhibits channels that determine the path of the pressurized gas through the inhaler into the mouthpiece. In the space for holding the powder formulation that has been provided for dispersing, the powder can lie loose or else it is located in a container, e.g., in a capsule or a blister, which, before the compressed gas is directed through it, is opened in such a way that the compressed gas can carry the powder along with almost no residues. In the case of a disposable inhaler, it has no other provisioning for additional doses of the powder formulations. In the case of a device for multiple use, the inhaler can have one or more reservoirs for the powder formulation. Thus, the reservoir can simply be a space that contains the loose powder mixture, and measured quantities are transferred from there into the pulverization space. Alternatively, the reservoir can be a collection of capsules that are filled with the powder formulation and are brought into the pulverization chamber either mechanically or manually. Finally, the reservoir can also be a blister with numerous pouches for the powder formulation, whereby one of these pouches is then always brought into the pulverization space. Such reservoir systems and the transfer of the powder formulation from the reservoir into the nebulizing space are known from the state of the art, and for that reason they will not be dealt with in more detail here.

The dry powder inhaler according to the invention can have as the pressure medium system a compressed air cartridge, a cartridge filled with a gas other than air, e.g., nitrogen, carbon dioxide, a noble gas such as helium or argon, or even a fluorohydrocarbon, an alkane, etc. Advantageous are embodiments of the dry powder inhaler in which the pressure medium system is a system that draws in air from the surroundings and then delivers the air in target-precise fashion under compression and pressure towards the formulation that is to be nebulized. First, air as the carrier medium for the powder particles is certainly the most harmless medium for the patient. Second, it is easily available. The preferred embodiment of the dry powder inhaler takes the needed quantity of air from the surroundings, compresses it, and then uses it as the carrier medium for the powder formulation. Replacement of the pressure medium system, as would be the case with a pressure medium stored in a cartridge, is dispensed with.

However, other embodiments of the dry powder inhaler in which the pressure medium system includes a cartridge that supplies a pressurized pressure medium can also be advantageous. In contrast to the dry powder inhaler described above, this embodiment is less complex in its design and therefore more cost-effective and smaller in its dimensions.

In every case, the pressure medium system is one such that the user of the inhaler can generate discharge of the pressure medium in a purposeful fashion.

Advantageous are embodiments of the dry powder inhaler that are characterized in that the device for provisioning the powder formulation is placed between the pressure medium system and the nozzle in such a way that the pressure medium must pass through the device, whereby preferably the device for provisioning the powder formulation exhibits a capsule filled with powder. Preferred embodiments of the dry powder inhaler are those in which the capsules are replaceable as expendable items. In this regard, a mechanism is provided on the dry powder inhaler with which the replacement of a capsule can be carried out.

In this embodiment, the pressure medium flows through the device for provisioning the powder formulation and distributes or assimilates the powder so that the desired aerosol is available after the provisioning chamber flow-through.

Advantageous are embodiments of the dry powder inhaler in which the device for provisioning the powder formulation includes a multidose blister container. Such multidose blister containers can be executed in linear fashion as a blister strip, flat, as blister disks or blister rings, or three-dimensionally as cylinder bodies or polyhedrons. Such multidose systems can contain 2 to 90 doses, preferably 5 to 60 doses, in particular, 7 to 30 doses, whereby each dose is stored in a separate blister pouch that is opened for use by means of a suitable device.

As has already been mentioned, dry powder inhalers in which air is provided as the pressure medium are preferred.

If the pressure medium system does not have to be operated manually as a matter of principle, but instead exhibits an actuator—in the form of an actuator valve, for example—through the opening or closing of which the pressure medium is released, those embodiments of the dry powder inhaler are advantageous that provide in the mouthpiece a flow rate sensor that measures the patient's inhalation flow and, beginning at a predetermined value, generates an input signal for the pressure medium system or its actuator.

The flow rate sensor measures the air stream when the patient inhales, and generates an input signal with which the actuator is contacted. The latter opens and allows the pressure medium to flow out if the flow rate lies within a range that is suitable for the inhalation, whereby the actuator does not release the pressure medium system if this flow rate lies outside the preferred range. This automatic opening and closing saves the providing of an additional actuating device, and ensures better ease of operation and easier handling of the inhaler.

The dry powder inhaler according to the invention has the following advantages when compared with the state of the art:

- An aerosol is created from powder bulk product that has been predosed in a suitable container, whereby energy that is present in the form of a pressurized gas is used for overcoming the agglomeration forces of the micronized powder particles among one another, so that an aerosol with a comparatively above-average high fraction of solid particles smaller than 5.8 µm is created.
- The system described here does not have to use fluorinated propellant gases or fluorochlorohydrocarbons.
- The creation of the aerosol and the particle size distribution that is achieved are independent of the patient's breathing maneuver.
- The powder residues in the device are minimal because of the design, since the deagglomeration of the powder is achieved through the action of the flowing gases in a nozzle, and not through impaction on collision surfaces.
- The described inhaler is small, and can easily be brought along by the patient.
- It is possible to forego the use of the device with a "spacer"—as used by other active dry powder systems (patent WO 99/6249)—since an aerosol cloud is created within the device by suitable provisions, and is slowly moved forward.

In the following, the invention is described in greater detail with the aid of several embodiments in accordance with the two drawing figures. The following are shown:

FIG. 1 A schematic representation of a first embodiment of a dry powder inhaler in a cutaway side view, FIG. 2 A schematic representation of a nozzle of a second embodiment of a dry powder inhaler in a cutaway side view, FIG. 3a A schematic representation of a first embodiment of a multidose blister container for provisioning of the powder formulation in a side view, FIG. 3b A schematic representation of a second embodiment of a multidose blister container for provisioning of the powder formulation in a side view, FIG. 3c A schematic representation of a third embodiment of a multidose blister container for provisioning of the powder formulation in a side view, FIG. 3d A schematic representation of a fourth embodiment of a multidose blister container for provisioning of the powder formulation in a perspective view, FIG. 3e A schematic representation of a fifth embodiment of a multidose blister container for provisioning of the powder formulation in a perspective view, FIG. 4 A schematic representation of a nozzle of a third embodiment of a dry powder inhaler in a cutaway side view, FIG. 5 A schematic representation of a nozzle of a fourth embodiment of a dry powder inhaler in a cutaway side view, FIG. 6 A schematic representation of a first embodiment of a device for decelerating the aerosol flow in a cutaway side view, FIG. 7 A schematic representation of a second embodiment of a device for decelerating the aerosol flow in a cutaway side view.

In the following, the same parts are provided with the same reference symbols.

FIG. 1 shows a schematic representation of a first embodiment of a dry powder inhaler 1 for dispersing pharmaceutical drug formulations in a cutaway side view.

The dry powder inhaler 1 has a mouthpiece 2 at its upper end. It exhibits an auxiliary energy source in the form of a pressure medium system 3, whereby the pressure medium system 3 is equipped with a pump that is connected to the surroundings by means of a valve 4 and uses ambient air as the pressure medium 8. The air serves as a carrier medium for the powder particles 7, and is drawn in during the expansion phase through the valve 4 by a plunger 21 acted upon by force from a spring 20, and is compressed when the plunger moves upward. Replacement of the pressure medium system, as would be the case with a pressure medium stored in a cartridge, is dispensed with.

The pressure medium 8 leaves the pressure medium system 3 by means of an actuator or actuator valve 5. In the embodiment shown in FIG. 1, a flow rate sensor 19 is provided in the mouthpiece 2. The flow rate sensor 19 measures the air stream when the patient inhales—the flow rate—and generates an input signal with which the actuator valve 5 is contacted. It opens and allows the pressure medium 8 to flow out if the flow rate is in a range suitable for inhalation, whereby the actuator 5 closes the pressure medium system 3 if this flow rate is outside this preferred range. This automatic opening and closing ensures better ease of operation, and optimizes conditions during inhalation.

After leaving the pressure medium system 3, the pressure medium 8 flows through a device for provisioning 6 of the powder formulation 7. The device for provisioning 6 of the powder formulation 7 has available a capsule 15 filled with powder 7. The mechanism by means of which the replacement of the capsule can take place is not shown.

In this embodiment, the pressure medium 8 flows through the device for provisioning 6 of the powder formulation 7 and assimilates a portion of the powder 7 so that after flowing through the provisioning chamber, the desired aerosol 9 is present in such a way that the powder particles 7 are dispersed within the gaseous pressure medium 8.

After that, the aerosol 9 flows through the nozzle 10, whereby it first enters the narrowing inlet section 11, passes through the middle piece 13 in which the narrowest cross section 14 of the nozzle 10 is located, and then flows through the widening outlet section 12. This embodiment thus makes use of a Laval nozzle.

In conjunction with this, the aerosol 9 accelerates in the narrowing inlet section 11, whereby the gaseous pressure medium 8 is accelerated more strongly and carries along with it the powder particles 7 it contains, as a result of which the transport of the powder particles 7 takes place. The shear forces exerted on the particles 7 by the gaseous pressure medium 8 as a result of the higher speeds of the gas molecules 8 cause a breaking up of the particle aggregates/agglomerates 7 into smaller particles of less diameter, as a result of which a deagglomeration is achieved. The aerosol 9 reaches its highest speed in or after the narrowest cross section 14 of the nozzle 10, which is located in the middle piece 13.

FIG. 2 shows a schematic representation of a nozzle 10 of a second embodiment of a dry powder inhaler in a cutaway side view.

The prepared aerosol, which consists of the powder particles dispersed in the pressure medium as carrier medium and of the pressure medium itself, enters the continuously narrowing inlet section 11 of the nozzle 10, is accelerated, passes through the narrowest cross section 14, which is located in the middle piece 13, in order then to flow though the widening outlet section 12 and leave the nozzle 10 through the outlet 17.

The Laval nozzle 10 shown in FIG. 2 is characterized in that it has a comparatively long outlet section 12, which has only a small angle of opening—approximately 11° in this case.

Such nozzles 10 are used in dry powder inhalers in which the aerosol flow in the nozzle 10 is accelerated to supersonic speed, whereby a Mach shock—not shown—forms in the widening outlet opening 12 of the nozzle 10. The described shaping of the nozzle 10 is required in order to accelerate the aerosol flow to supersonic speed and ensure the formation of the Mach disk in the outlet section 12.

When the gas molecules go through this Mach shock zone, they are strongly decelerated from supersonic to subsonic speed within the space of a few tenths of a millimeter. The powder particles, which, before the Mach shock, were slower than the gas molecules, are less strongly decelerated than the gas molecules so that after the Mach shock, the powder particles have a higher speed than the gas molecules. This results in extremely high frictional and shear forces, which act on the powder particles and deagglomerate them.

FIG. 3a shows a schematic representation of a first embodiment of a multidose blister container 22 for provisioning of the powder formulation in a side view. The multidose blister container 22 is designed in linear fashion as a blister strip 23, and has available several capsules 26, which are arranged in a row and each capsule 26 of which contains a single dose, whereby the particular capsule 26 is opened for use by means of a suitable device (not shown).

FIG. 3b shows a schematic representation of a second embodiment of a multidose blister container 22 for provisioning of the powder formulation in a side view. The multidose blister container 22 is designed flat as a blister disk 24, and has available a multiplicity of capsules 26 that are arranged in a circle.

FIG. 3c shows a schematic representation in a side view of a third embodiment of a multidose blister container 22 for provisioning of the powder formulation. The multidose blister container 22 is designed flat as a blister ring 25, and has available a multiplicity of capsules 26 that are arranged in a circle.

FIG. 3d shows a schematic representation in a perspective view of a fourth embodiment of a multidose blister container 22 for provisioning of the powder formulation. The multidose blister container 22 is executed three-dimensionally as a cylindrical body. Such multidose systems can contain 2 to 90 doses, preferably 5 to 60 doses, in particular, 7 to 30 doses, whereby each dose is stored in a separate capsule 26 that is opened for use by means of a suitable device.

FIG. 3e shows a schematic representation in a perspective view of a fifth embodiment of a multidose blister container 22 for provisioning of the powder formulation. The multidose blister container 22 is—as in FIG. 3d—executed three-dimensionally in the form of a polyhedron.

FIG. 4 shows a schematic representation of a nozzle 10 of a third embodiment of a dry powder inhaler in a cutaway side view. This is an aperture plate 28, which has available neither a narrowing inlet section nor a widening outlet section.

FIG. 5 shows a schematic representation of a nozzle 10 of a fourth embodiment of a dry powder inhaler in a cutaway side view. This is an aperture plate 28, which has a narrowing inlet section 11 available, but not a widening outlet section.

Figure 1:
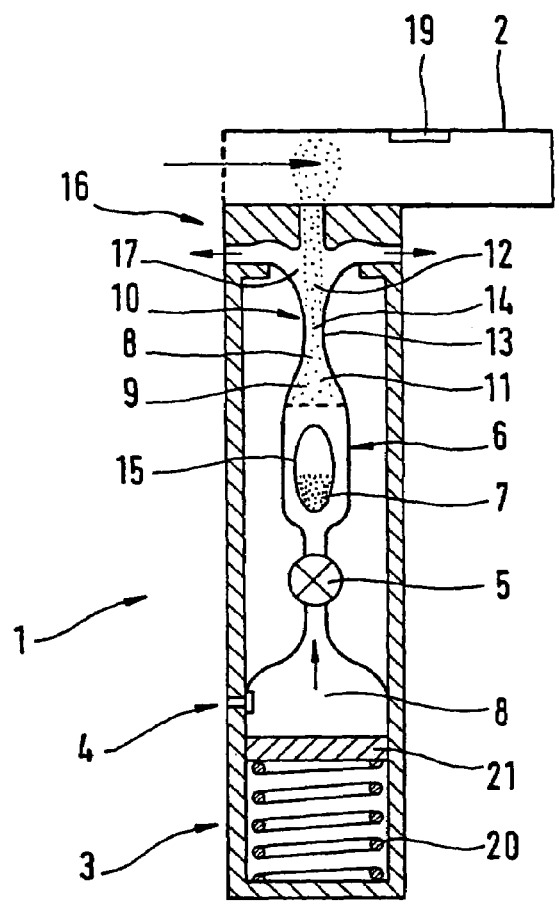
Figure 2:
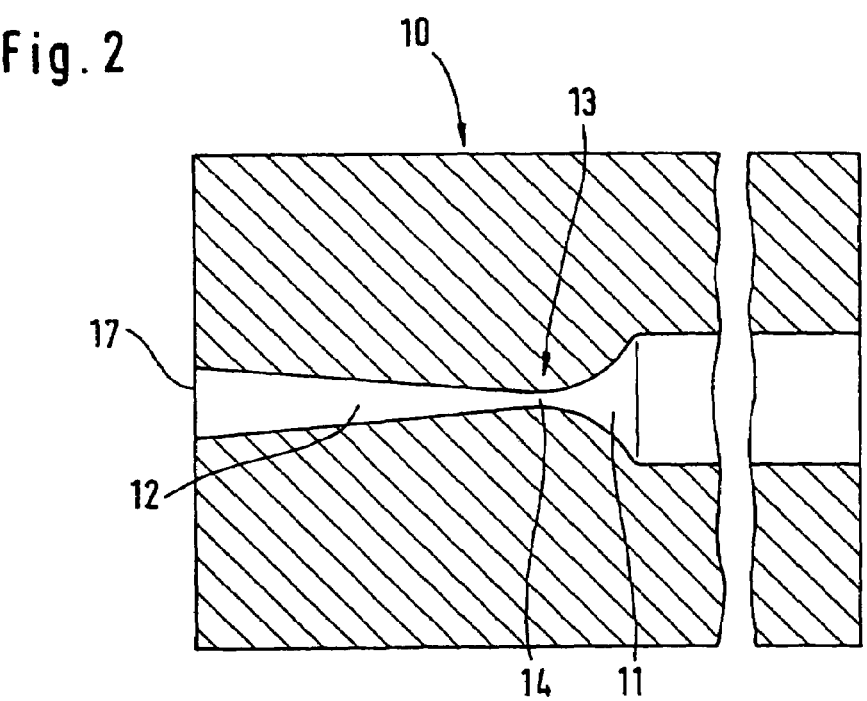
Figure 6:
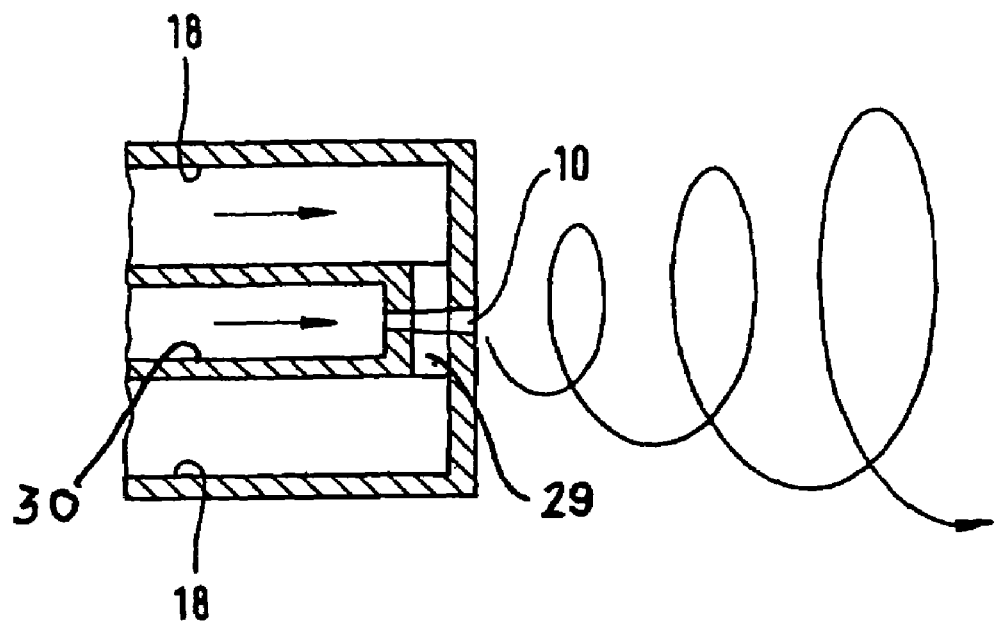

FIG. 6 shows a schematic representation of a first embodiment of a device for decelerating the aerosol flow in a cutaway side view. The two flows, i.e., both the inhalation air flow in the inlet channel 18 and the aerosol flow in channel 30, first run parallel in two tubes that are coaxial with each other, whereby the inhalation air is transformed into a swirling flow. The aerosol flow that is injected into this swirling flow exhibits a reduced flow speed.

Figure 7:
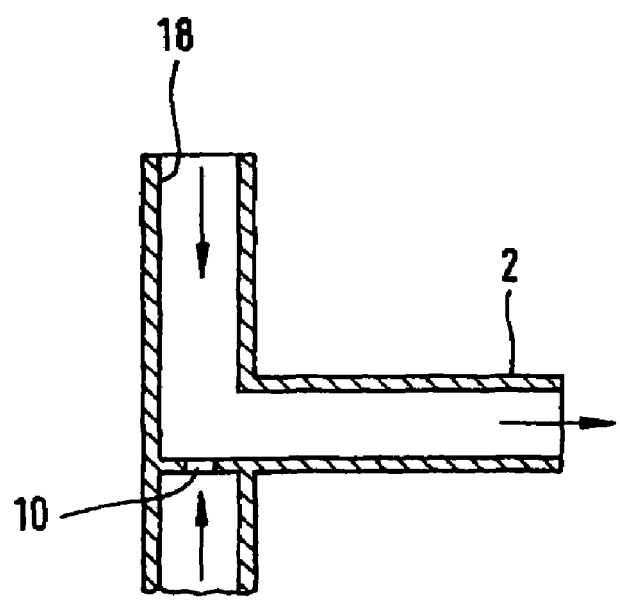

FIG. 7 shows a schematic representation of a second embodiment of a device for decelerating the aerosol flow in a cutaway side view. The inhalation air flow and the aerosol flow are directed towards each other. When they meet, and as a result of the deflection of the flow, the forward speed of the aerosol flow is reduced.

| List of Reference Symbols | |
|---|---|
| 1 | Powder inhaler |
| 2 | Mouthpiece |
| 3 | Pressure medium system |
| 4 | Valve |
| 5 | Actuator valve |
| 6 | Device for provisioning |
| 7 | Powder formulation |
| 8 | Gaseous pressure medium |
| 9 | Aerosol |
| 10 | Nozzle |
| 11 | Inlet section |
| 12 | Outlet section |
| 13 | Middle piece |
| 14 | Narrowest cross section |
| 15 | Capsule |
| 16 | Device |
| 17 | Outlet opening of the nozzle |
| 18 | Inlet channel |
| 19 | Flow rate sensor |
| 20 | Spring |
| 21 | Plunger |
| 22 | Multidose blister container |
| 23 | Blister strip |
| 24 | Blister disk |
| 25 | Blister ring |
| 26 | Capsule |
| 27 | Blister body |
| 28 | Aperture plate |
| 29 | Swirl chamber |
| 30 | Channel |

The invention claimed is:

1. A dry powder inhaler, comprising: a mouthpiece for dispersing pharmaceutical drug formulations, a Laval nozzle communicating with the mouthpiece, an inlet channel, whereby inhalation air is drawn in through the inlet channel, and a swirling flow of the inhalation air is created between the inlet channel and the mouthpiece, a multidose blister container for supplying a powder formulation in communication with the Laval nozzle, and an auxiliary energy source in the form of a pressure medium system in communication with the multidose blister container for supplying the powder formulation, wherein upon activation of the pressure medium system, a gaseous pressure medium is released into the multidose blister container for supplying the powder formulation, and forms an aerosol with the powder formulation in such a way that powder particles are present in dispersed form within the gaseous pressure medium prior to entering the Laval nozzle, entering the mouthpiece, and leaving the dry powder inhaler.

2. The dry powder inhaler according to claim 1, characterized in that a narrowest cross section of the Laval nozzle is about 100 μm to 1500 μm.

3. The dry powder inhaler according to claim 1, characterized in that the pressure medium system includes a pump that uses ambient air as the gaseous pressure medium.

4. The dry powder inhaler according to claim 1, characterized in that the pressure medium system includes a cartridge that stores the pressure medium.

5. The dry powder inhaler according to claim 4, characterized in that air, N2, CO2, Ar, or He is provided as the pressure medium.

6. The dry powder inhaler according to claim 1, characterized in that the multidose blister container for supplying the powder formulation is placed between the pressure medium system and the Laval nozzle in such a way that the pressure medium must pass through the device.

7. The dry powder inhaler according to claim 1, characterized in that the multidose blister container for supplying the powder formulation comprises a capsule filled with powder.

8. The dry powder inhaler according to claim 1, wherein the mouthpiece comprises a flow rate sensor that generates an input signal for the pressure medium system.

9. The dry powder inhaler according to claim 1, characterized in that the Laval nozzle and an inlet channel for inhalation air are arranged in such a way that an aerosol flow leaving the Laval nozzle and the inhalation air are directed in opposite directions.

10. The dry powder inhaler according to claim 1, characterized in that the Laval nozzle and an inlet channel for inhalation air are arranged in such a way that an aerosol flow leaving the Laval nozzle and the inhalation air collide with each other at an angle.

11. The dry powder inhaler according to claim 1, characterized in that a channel that guides an aerosol flow and the inlet channel for the inhalation air empty into a swirl chamber, whereby the aerosol is directed from the swirl chamber to the Laval nozzle.

12. A dry powder inhaler, comprising: a mouthpiece for dispersing pharmaceutical drug formulations, a Laval nozzle communicating with the mouthpiece, an inlet channel, whereby inhalation air is drawn in through the inlet channel, and a swirling flow of the inhalation air is created between the inlet channel and the mouthpiece, a multidose blister container for supplying a powder formulation in communication with the Laval nozzle, and an auxiliary energy source in the form of a pressure medium system in communication with the multidose blister container for supplying the powder formulation, wherein upon activation of the pressure medium system, a gaseous pressure medium is released into the multidose blister container for supplying the powder formulation, and forms an aerosol with the powder formulation in such a way that powder particles are present in dispersed form within the gaseous pressure medium prior to entering the Laval nozzle, entering the mouthpiece, and leaving the dry powder inhaler.

13. The dry powder inhaler according to claim 12, characterized in that the Laval nozzle and an inlet channel for inhalation air are arranged in such a way that an aerosol flow leaving the Laval nozzle and the inhalation air are directed in opposite directions.

14. The dry powder inhaler according to claim 12, characterized in that a channel that guides an aerosol flow and inlet channels for inhalation air empty into a swirl chamber, whereby the aerosol is directed from the swirl chamber to the Laval nozzle.

15. A dry powder inhaler, comprising: a mouthpiece for dispersing pharmaceutical drug formulations, a Laval nozzle communicating with the mouthpiece, an inlet channel, whereby inhalation air is drawn in through the inlet channel, and a swirling flow of the inhalation air is created between the inlet channel and the mouthpiece, a multidose blister container for supplying a powder formulation in communication with the Laval nozzle, and an auxiliary energy source in the form of a pressure medium system in communication with the multidose blister container for supplying the powder formulation, wherein: the mouthpiece comprises a flow rate sensor that generates an input signal for the pressure medium system, and upon activation of the pressure medium system, a gaseous pressure medium is released into the multidose blister container for supplying the powder formulation, and forms an aerosol with the powder formulation in such a way that powder particles are present in dispersed form within the gaseous pressure medium prior to entering the Laval nozzle, entering the mouthpiece, and leaving the dry powder inhaler.

16. The dry powder inhaler according to claim 15, characterized in that the Laval nozzle and an inlet channel for inhalation air are arranged in such a way that an aerosol flow leaving the Laval nozzle and the inhalation air are directed in opposite directions.

17. The dry powder inhaler according to claim 15, characterized in that a channel that guides an aerosol flow and inlet channels for inhalation air empty into a swirl chamber, whereby the aerosol is directed from the swirl chamber to the Laval nozzle.

18. A dry powder inhaler, comprising: a mouthpiece for dispersing pharmaceutical drug formulations, a Laval nozzle communicating with the mouthpiece, an inlet channel, whereby inhalation air is drawn in through the inlet channel, and a swirling flow of the inhalation air is created between the inlet channel and the mouthpiece, the Laval nozzle including a narrowing inlet section, a section of narrowest cross-section, and a widening outlet section, a device for supplying a powder formulation in communication with the Laval nozzle, an auxiliary energy source in the form of a pressure medium system in communication with the device for supplying the powder formulation, wherein: upon activation of the pressure medium system, a gaseous pressure medium is released into the device for supplying the powder formulation, and forms an aerosol with the powder formulation in such a way that powder particles are present in dispersed form within the gaseous pressure medium prior to entering the Laval nozzle, and the powder particles achieve a supersonic speed at an end of the narrowing inlet section of the Laval nozzle and are decelerated to subsonic speed in the widening outlet section of the Laval nozzle.

19. The dry powder inhaler according to claim 18, characterized in that a narrowest cross section of the Laval nozzle is about 100 μm to 1500 μm.

* * * * *